United States Patent [19]

Ellestad et al.

[11] 4,351,329
[45] Sep. 28, 1982

[54] HIGH FREQUENCY BREATH PUMP

[75] Inventors: Raymond A. Ellestad, Rialto; Harold U. Bartels, Riverside, both of Calif.

[73] Assignee: Bear Medical Systems, Inc., Riverside, Calif.

[21] Appl. No.: 204,435

[22] Filed: Nov. 6, 1980

[51] Int. Cl.³ .................................... A61M 16/00
[52] U.S. Cl. .................... 128/204.21; 128/205.24; 128/205.14
[58] Field of Search ................ 128/204.21, 204.24, 128/204.25, 205.11, 205.13, 205.14, 205.15, 205.16, 205.18, 205.19, 205.24, 203.12, 910, 203.28

[56] References Cited

U.S. PATENT DOCUMENTS

| | | | |
|---|---|---|---|
| 3,033,195 | 5/1962 | Gilroy et al. | 128/205.15 |
| 3,523,527 | 8/1970 | Foster | 128/204.21 |
| 3,621,842 | 11/1971 | Manley | 128/204.25 |
| 3,754,550 | 8/1973 | Kipling | 128/205.16 |
| 3,921,628 | 11/1975 | Smythe et al. | 128/204.21 |

FOREIGN PATENT DOCUMENTS 2035829  1/1972  Fed. Rep. of Germany ....................... 128/205.14

Primary Examiner—Henry J. Recla

[57] ABSTRACT

A system for sequentially providing a volume of gas containing a high frequency oscillation to a proximal airway. In a preferred embodiment a control means periodically drives in synchronism both inhalation and exhalation means into an inspiratory phase of an oscillatory cycle and then into an expiratory phase of the oscillatory cycle. The inhalation means during the inspiratory phase delivers a volume of fresh gas to the proximal airway of a patient, and during the expiratory phase refills itself from a source of low pressure gas while simultaneously blocking therefrom expired gas from the proximal airway. The exhalation means during the inspiratory phase vents to atmosphere expired gas withdrawn from the proximal airway during the previous expiratory phase and simultaneously blocks therefrom fresh gas from said inhalation means and during the expiratory phase extracts the expired volume of gas from the proximal airway.

6 Claims, 1 Drawing Figure

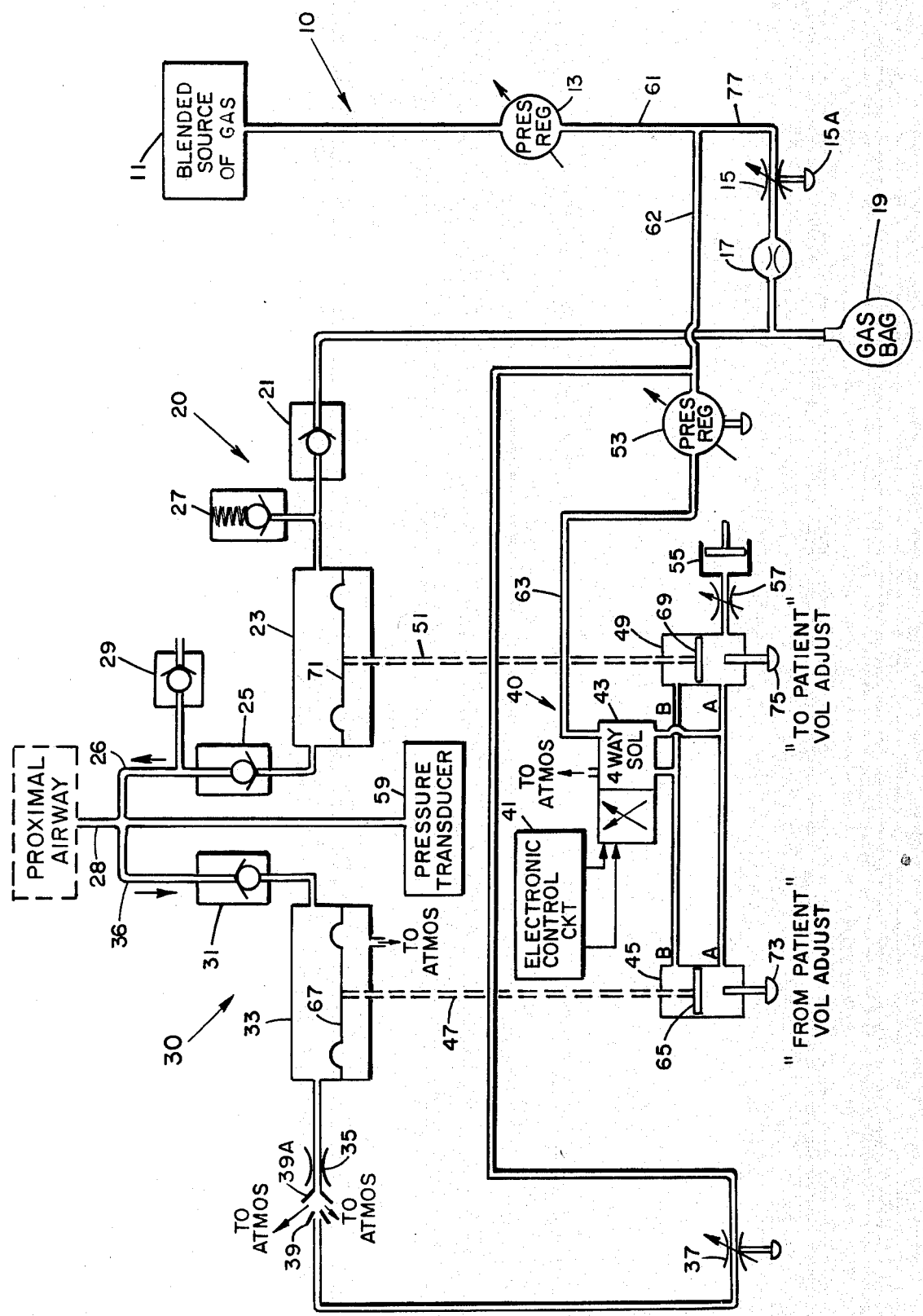

HIGH FREQUENCY BREATH PUMP

BACKGROUND OF THE INVENTION

1. Field of the Invention

This invention relates to a high frequency positive pressure breathing or oscillatory system, that includes a dual drive system, which oscillatory system moves moderate volumes of a breathing gas in and out of a patient circuit at high frequencies, while at the same time continuously bringing in fresh gas from a source.

2. Description of the Prior Art

Three functions are considered essential to the successful use of a high frequency positive pressure breathing modality. These essential functions are:

(1) Provide a continuous amount of fresh gas to the patient (for removal of $CO_2$ and to provide $O_2$).
(2) Actively withdraw gas from the patient during the expiratory phase or portion of a breathing cycle.
(3) Deliver controlled volumes of gas to the patient at high frequency.

A novelty search conducted in the United States Patent and Trademark Office to locate patents relevant to high frequency positive pressure breathing systems resulted in the discovery of the following relevant patents:

| U.S. Pat. No. | Title | Inventor |
|---|---|---|
| 2,918,917 | Apparatus for Vibrating Portions of a Patient's Airway | Emerson |
| 3,349,766 | Anesthetizing, Resuscitating, and Respiratory Apparatus | Donofrio |
| 3,810,719 | Pump for Discharging a Predetermined Quantity of Fluid | Wolthers |
| 3,863,082 | Permanent Magnet Translational Motor with Auxiliary Electromagnet | Gillott et al |
| 3,923,055 | Process and Device for Controlling the Pressure Course of a Respirator | Hammacher |
| 3,993,059 | Device for Ventilating a Patient | Sjostrand |
| 4,155,356 | Respiration Assisting Apparatus and Method | Venegas |
| 1,553,379 (U.K.) | Improvements in or Relating to Respirators | |

The fields of search were:

| Class | Subclass |
|---|---|
| 92 | 13.1 and 13.2 |
| 128 | 204.18, 204.21, 204.26, 205.14 and 205.24 |
| 417 | 338, 339, 342, 343, 394, 395, 400 and 403 |

Some of these patents disclose systems that perform, in some manner, one or two of the above-noted three essential functions. However, none of these patents teach or even suggest a system which performs all of these three essential functions.

SUMMARY OF THE INVENTION

Briefly, a high frequency positive pressure breathing system is provided which performs all three of the above-identified essential functions by moving moderate volumes of a breathing gas in and out of a patient circuit at high frequencies while at the same time continuously bringing in fresh gas from a source.

In a preferred embodiment, inhalation and exhalation means are periodically driven in synchronism into the inspiratory and expiratory phases of an oscillatory cycle by a control means. During the inspiratory phase, the inhalation means delivers a volume of fresh gas to the proximal airway of a patient while the exhalation means blocks therefrom the volume of fresh gas being delivered by the inhalation means to the proximal airway and simultaneously vents to atmosphere a volume of expired gas withdrawn from the proximal airway during the previous expiratory phase. During the expiratory phase, the inhalation means refills itself from a source of low pressure gas while simultaneously blocking therefrom the expired volume of gas from the proximal airway while the exhalation means extracts the expired volume of gas from the proximal airway.

It is therefore an object of this invention to provide an improved breath pump.

Another object of this invention is to provide a controlled volume high frequency breath pump.

A further object of this invention is to provide a high frequency positive pressure breathing system which moves moderate volumes of gas in and out of the proximal airway of a patient at high frequencies while at the same time continuously bringing in fresh gas from a source.

BRIEF DESCRIPTION OF THE DRAWING

These and other objects, features and advantages of the invention, as well as the invention itself, will become more apparent to those skilled in the art in the light of the following detailed description taken in consideration with the accompanying drawing which illustrates a block diagram of a preferred embodiment of the invention.

DESCRIPTION OF THE PREFERRED EMBODIMENT

Referring now to the drawing, a block diagram of a preferred embodiment of the invention, a high frequency positive pressure breathing system, is disclosed for moving moderate volumes of a gas in and out of a patient circuit at high frequencies, while at the same time continuously bringing in fresh gas from a source.

Basically, the illustrated system may be broken down into the following functional units:

1. A regulated source 10 of low and high pressure fresh gas. The high pressure gas is used for control purposes, while the low pressure gas is the fresh gas that is ultimately used by a patient. The regulated source 10 is comprised of a high pressure gas source 11, a pressure regulator 13, a variable or controllable orifice 15, a flow meter 17 and a gas bag 19. The gas from the source 11 can be, for example, air, oxygen, a combination of air and oxygen, or a combination of air and anesthesia gas.

2. An inhalation means 20 for applying a volume of fresh gas to the proximal airway of a patient. The inhalation means 20 is comprised of a check valve 21, a diaphragm pump 23 and a check valve 25. The check valve 25 is located in an inspiratory conduit 26 coupling the pump 23 to a main breathing conduit 28 adapted for connection to the proximal airway of a patient. A relief valve 27 and a safety valve 29 may be included in the inhalation means 20.

3. An exhalation means 30 for selectively withdrawing a volume of expired gas from the proximal airway and operating as an exhalation valve to vent that expired volume of gas to atmosphere. The exhalation means 30 is comprised of a check valve 31, a diaphragm pump 33 and an orifice or restrictor 35. The check valve 31 is located in an expiratory conduit 36 coupling the pump 33 to the main breathing conduit 28. An adjustable PEEP (Positive End Expiratory Pressure) control valve 37 and a PEEP jet and venturi 39 may be included in the exhalation means 30.

4. A control means 40 for synchronously driving the inhalation and exhalation means into an inspiratory phase of an oscillatory cycle and then both of them into an expiratory phase of the oscillatory cycle. The control means 40 is comprised of an electronic control circuit 41, a 4-way solenoid 43, a first high pressure drive cylinder 45 and an associated shaft 47, and a second high pressure drive cylinder 49 and an associated shaft 51. A pressure regulator 53, adjustable cylinder 55, variable orifice or restrictor 57 and pressure transducer 59 may be included in the control means 40.

For an understanding of the system of the invention, the operation of each of the above-identified functional units in that system will now be discussed.

The pressure of gas from the high pressure gas source 11 is regulated by the pressure regulator 13. Regulated, high pressure gas from regulator 13 is applied through air tubes or ducts 61 and 62, the regulator 53 and air tube 63 to an input port of the 4-way solenoid 43 in the control means 40. The pressure regulator 53 determines the maximum pressure of the gas being applied to the input port of the solenoid 43. A second port of the control means 40 is vented to atmosphere as shown in the figure.

The electronic control circuit 41, which may be a synchronized multivibrator or any other suitable source of electrical pulses, develops alternate pulses over two output lines to control the operation of the solenoid 43.

It should be noted at this time that the shaft 47 is attached between piston 65 of cylinder 45 and a diaphragm 67 in pump 33. Similarly, the shaft 51 is attached between piston 69 of cylinder 49 and a diaphragm 71 in a pump 23.

Assume that a pulse is applied to the solenoid 43 from the lower output line of the circuit 41, causing the solenoid 43 to be in the position as shown. In this position, high pressure gas from regulator 13 is passed through the solenoid 43 to ports A in drive cylinders 45 and 49, while ports B in drive cylinders 45 and 49 are vented to atmosphere through the solenoid 43. The high pressure gas being applied to the A ports simultaneously forces pistons 65 and 69 upward. The upward movement of piston 45 causes the shaft 47 to move the diaphragm 67 upward. In a like manner, the upward movement of the piston 67 causes the shaft 51 to move the diaphragm 71 upward. The upward movement of the respective diaphgrams 67 and 71 of the pumps 33 and 23 initiates the inspiratory phase of an oscillatory cycle.

When an alternate pulse is applied to the solenoid 43 from the upper output line of the circuit 41, the operation of the solenoid 43 reverses. At this time the high pressure gas from the regulator 13 is routed through the solenoid 43 to the B ports of the cylinders 45 and 49, while the A ports in the cylinders 45 and 49 are vented to atmosphere through the solenoid 43. In this reversed operation, high pressure gas being applied to the B ports forces the pistons 65 and 69 downward until they come to stop positions determined by the settings of "from patient" and "to patient" volume adjust controls 73 and 75, respectively. The controls 73 and 75 may be screw adjustments.

The downward movement of the pistons 65 and 69 cause the shafts 47 and 51 to respectively move the diaphragms 67 and 71 downward to initiate the expiratory phase of an oscillatory cycle.

It can thus be seen that, since the pistons 65 and 69 move up and down in synchronism, the diaphragms 67 and 71 of diaphragm pumps 33 and 23, respectively, move up in synchronism during an inspiratory phase of an oscillatory cycle and down in synchronism during an expiratory phase of an oscillatory cycle. The frequency of the electro-mechanically produced oscillatory cycles depends upon the pulse repetition rate of the pulses developed by the electronic control circuit 41 to control the operation of the 4-way solenoid 43. The pulse repetition rate of a train of pulses from circuit 41 may be within the range of 5 to 50 hertz (Hz). Typically, the pulse repetition rate of the train of pulses may be 15 Hz. An adjustable control (not shown) on the electronic control circuit 41 would normally be used to control the pulse repetition rate of an output train of pulses. As indicated before, the volume of fresh gas being applied to the proximal airway during the inspiratory phase is controlled by the volume adjustment control 75. Control 75 controls the maximum travel distance of piston 69 which, by means of shaft 51 and diaphragm 71, controls the volume displacement of the pump 23. In a similar manner the volume adjustment control 73 controls the maximum travel distance of piston 65 which, by means of shaft 47 and diaphragm 67, controls the volume displacement of the pump 33. The trapping efficiency at the proximal airway would determine the adjustments of the controls 73 and 75. For given settings of the controls 73 and 75, the pressure transducer 59, which is coupled to the main breathing conduit 28, would indicate the magnitude of pressure oscillation at the proximal airway for a given volume of fresh gas being delivered to the proximal airway during the inspiratory phase of an oscillatory cycle.

The operation of the inhalation means 20 will now be discussed. High pressure gas from the regulator 13 passes through the tube 61, through a branch 77 of the tube 62 and into the variable or controllable orifice 15. A flow control valve 15A is used to vary the size of the orifice 15 to lower the pressure of the gas and to control the flow rate of the gas as monitored by the flowmeter 17. Gas from flowmeter 17 can either go to fill the bag 19 or flow through check valve 21, depending upon whether the diaphragm 71 of pump 23 is moving up during the inspiratory phase or down during the expiratory phase.

As the diaphragm 71 of pump 23 is moving up during the inspiratory phase, gas in the pump 23 is forced through check valve 25 to the proximal airway of the patient via the inspiratory conduit 26 and the breathing conduit 28. At the same time check valve 21 is biased closed by the increased gas pressure. Therefore, no gas from the pump 23 can go backward through check valve 21 to the bag 19. The setting of relief valve 27 determines the maximum pressure that can be applied to close the valve 21. Any excess pressure over that maximum pressure is vented to atmosphere through relief valve 27. Since check valve 21 is biased closed during the inspiratory phase, gas from regulator 13 flows into the bag 19 to refill it.

As the diaphragm 71 moves down during the expiratory phase, check valve 25 is biased closed and check valve 21 is opened. Therefore, because valve 25 is closed, the pump 23 will not draw any expired gas from the proximal airway. Instead, the pump 23 draws fresh gas through open check valve 21 from the gas bag 19.

When gas is delivered to the proximal airway during the inspiratory phase, that gas is prevented from being vented to atmosphere by operation of the expiratory means 30. As discussed before, diaphragm 67 of pump 33 moves up at the same time that diaphragm 71 of pump 23 moves up. As diaphragm 67 moves up, the pressure inside of pump 33 rises. This is due to the restrictor 35 which limits the rate at which previously expired gas in the pump 33 is vented to atmosphere. This increase in pressure in pump 33 biases check valve 31 closed during the inspiratory phase. So pump 33 is venting expired gas to atmosphere at the same time that it is providing a back bias to close check valve 31. Thus, during the inspiratory phase, the fresh gas driven by pump 23 through check valve 25 can only go to the proximal airway.

As the diaphragms 67 and 71 of the pumps 33 and 23, respectively, are moving down in synchronism during the expiratory phase, check valve 25 is closed and check valves 31 and 21 are opened. This allows pump 33 to pull expired gas out of the proximal airway, via the breathing conduit 28 and the expiratory conduit 36, at the same time that pump 23 is getting fresh air from the gas bag 19. No expired gas is applied to pump 23 because valve 25 is closed when diaphragm 71 is moving down. Thus, expired gas can only go through open valve 31 into pump 33 during the expiratory phase of a breathing cycle. Valve 29 operates as a safety valve to open to atmosphere if any excess negative pressure is drawn in the proximal airway by the returning diaphragm.

The above-described cycle of operation is repeated at the frequency determined by the electronic control circuit 41.

To provide a static unidirectional pressure level of expired gas being vented to atmosphere, the PEEP jet and venturi 39 is used. High pressure gas from the regulator 13 is applied through tubes 61 and 62 and through the variable PEEP control valve 37 to the PEEP jet and venturi 39. The PEEP jet and venturi 39 is basically a high pressure gas jet blowing at a venturi. This gas jet creates a pressure in a chamber 39A through which the expired gas from the restrictor 35 must pass before it is vented to atmosphere. As a result, the gas being vented through the restrictor 35 and chamber 39A has to work against the gas pressure from the PEEP jet and venturi. This results in an increase in the pressure level in the chamber 39A, closing check valve 31 and creating a static unidirectional pressure level in the proximal airway.

An adjustable cylinder 55 may be connected to cylinders 45 and 49 through variable restrictor or orifice 57 to provide waveform shaping. If the cylinder 55 has a large compliance, some of the gas that flows from solenoid 43 into the cylinders 45 and 49 would flow into the adjustable cylinder 55. As a result, the pressure would gradually, rather than suddenly, rise to a relatively high level in the high pressure cylinders 45 and 49. This adjustable cylinder 55 can, therefore, adjust the pressure rise of the gas over a given range. On the other hand, the cylinder 55 and orifice 57 may be omitted entirely to enable the pressure in the cylinders 45 and 49 to suddenly rise, if so desired.

The invention thus provides a high frequency positive pressure breathing system that includes a dual drive system operated in synchronism for moving moderate volumes of gas in and out of a patient circuit at high frequencies, while at the same time continuously bringing in fresh gas from a source.

While the salient features of the invention have been illustrated and described in a preferred embodiment of the invention, it should be readily apparent to those skilled in the art that various changes and modifications can be made within the spirit and scope of the invention as set forth in the appended claims.

What is claimed and desired to be secured by Letters Patent of the United States is:

1. Apparatus for pumping breathable gas from a pressurized source into and out of the proximal airway of a patient, comprising:
   conduit means adapted for fluid connection to said proximal airway;
   inhalation means, fluidly connected between said source and said conduit means, for alternately (a) receiving a first selected volume of gas from said source during an expiratory phase of the respiratory cycle of said patient, and (b) delivering said first selected volume of gas to said conduit means during the subsequent inspiratory phase of the respiratory cycle;
   exhalation means, fluidly connected to said conduit means, for alternately (a) withdrawing a second selected volume of gas from said conduit means during an expiratory phase of said respiratory cycle, and (b) venting said second selected volume of gas to atmosphere during the next inspiratory phase of said respiratory cycle;
   driving means for driving in synchronism both of said inhalation and exhalation means alternately forcing gas therefrom during a corresponding inspiratory phase and drawing gas thereto during a corresponding expiratory phase; and
   volume adjustment means for independently adjusting said first and second selected volumes.

2. The apparatus of claim 1, further comprising:
   control means for adjusting the frequency with which said driving means alternately drives said inhalation and exhalation means.

3. The apparatus of claim 1, wherein said inhalation means includes a first bidirectional gas pump, said exhalation means includes a second bidirectional gas pump, and said driving means comprises:
   first and second pneumatic cylinders, said first cylinder having a first piston operatively connected to said first pump and said second cylinder having a second piston operatively connected to said second pump;
   means for generating pulses at a preselected pulse repetition rate;
   a source of high pressure gas; and
   means responsive to said pulses for alternately routing gas from said high pressure gas source along a first path to said first and second cylinders to cause said first and second pistons to operate said first and second pumps in a first direction and along a second path to said first and second cylinders to cause said first and second pistons to operate said first and second pumps in a second direction.

4. The apparatus of claim 3, further comprising: means for adjusting said pulse repetition rate.

5. The apparatus of claim 3, wherein said first and second pistons are respectively connected to said first and second pumps in a manner such that said first and second preselected volumes are proportional to the length of travel of said first and second pistons, respectively, and wherein said volume adjustment means comprises:
  first and second means for independently adjusting the length of travel of said first and second pistons, respectively.

6. The apparatus of claim 3, wherein said driving means further comprises:
  means pneumatically coupled to said first and second cylinders for creating a variable measurable rise time for the pneumatic pressure in said first and second cylinders resulting from the routing thereto of gas from said high pressure gas source, thereby to modulate the operation of said first and second pumps through said first and second pistons.

* * * * *